(12) United States Patent
Xu et al.

(10) Patent No.: US 9,758,440 B2
(45) Date of Patent: Sep. 12, 2017

(54) METHOD AND DEVICE FOR CATALYTIC METHANATION OF SYNTHESIS GAS

(71) Applicants: INSTITUTE OF PROCESS ENGINEERING, CHINESE ACADEMY OF SCIENCES, Beijing (CN); CHINA KINGSUN MATERIAL TECHNOLOGY CO., LTD, Zhangjiangang (CN)

(72) Inventors: Guangwen Xu, Beijing (CN); Jiao Liu, Beijing (CN); Dianmiao Cui, Beijing (CN); Jian Yu, Beijing (CN)

(73) Assignees: INSTITUTE OF PROCESS ENGINEERING, CHINESE ACADEMY OF SCIENCES, Beijing (CN); China Kingsun Material Technology Co., LTD, Zhangjiangang (CN)

( * ) Notice: Subject to any disclaimer, the term of this patent is extended or adjusted under 35 U.S.C. 154(b) by 19 days.

(21) Appl. No.: 14/907,726

(22) PCT Filed: Jul. 26, 2013

(86) PCT No.: PCT/CN2013/080236
§ 371 (c)(1),
(2) Date: Jan. 26, 2016

(87) PCT Pub. No.: WO2015/010342
PCT Pub. Date: Jan. 29, 2015

(65) Prior Publication Data
US 2016/0176774 A1    Jun. 23, 2016

(51) Int. Cl.
*C07C 1/04* (2006.01)
*C07C 1/12* (2006.01)
(Continued)

(52) U.S. Cl.
CPC .......... *C07C 1/0425* (2013.01); *B01J 8/0055* (2013.01); *B01J 8/388* (2013.01); *C01B 3/586* (2013.01);
(Continued)

(58) Field of Classification Search
None
See application file for complete search history.

(56) References Cited

U.S. PATENT DOCUMENTS

| | | | | |
|---|---|---|---|---|
| 3,351,564 A | * | 11/1967 | Faatz, Jr | C01B 3/025 252/372 |
| 5,827,902 A | * | 10/1998 | Maretto | C10G 2/342 518/700 |
| 8,980,195 B2 | * | 3/2015 | Pelton | C10J 3/485 422/214 |

OTHER PUBLICATIONS

Blum, D. B. et al. Advances in Chemistry Series (1975), 146 (Methanation Synth. Gas, Symp., 1974), 149-59.*

(Continued)

*Primary Examiner* — Medhanit Bahta
(74) *Attorney, Agent, or Firm* — Goldilocks Zone IP Law (57) ABSTRACT

The method for catalytic methanation of synthesis gas includes the following steps: 1) feeding the synthesis gas into the bottom of a reactor of an upward concurrent flow transporting bed so as to adequately mix and preheat with methanation catalyst entering the bottom of the reactor until the activation temperature of the catalyst is reached and then the methanation reaction begins; and 2) after the methanation reaction, immediately passing the product gas and the catalyst grains outputted from the transporting bed into a gas-solid separator to perform a rapid separation so as to obtain the product gas.

4 Claims, 4 Drawing Sheets

(51) Int. Cl.
    *C10L 3/08*     (2006.01)
    *B01J 8/38*     (2006.01)
    *B01J 8/00*     (2006.01)
    *C01B 3/58*     (2006.01)

(52) U.S. Cl.
    CPC ............ *C07C 1/042* (2013.01); *C07C 1/0415* (2013.01); *C10L 3/08* (2013.01); *B01J 2208/00141* (2013.01); *B01J 2208/00203* (2013.01); *C07C 1/12* (2013.01); *C10L 2290/54* (2013.01); *Y02P 20/124* (2015.11)

(56) References Cited

OTHER PUBLICATIONS

Trembly, J. P. et al. American Chemical Society, Division of Fuel Chemistry, Volume: 56, Issue: 1, pp. 247-248, Journal; 2011; Abstract.*

* cited by examiner

METHOD AND DEVICE FOR CATALYTIC METHANATION OF SYNTHESIS GAS

CROSS REFERENCE TO RELATED PATENT APPLICATIONS

This application claims the benefit under 35 U.S.C. Section 371, of PCT International Application No. PCT/CN2013/080236, filed Jul. 26, 2013, the disclosures of which are hereby incorporated by the references.

TECHNICAL FIELD

This present invention belongs to the field of process design and application of chemical reaction process, and particularly, relates to a method and a device for catalytic methanation of synthesis gas using a transporting bed with low pressure drop. The present invention further relates to a new process method for catalytic methanation of synthesis gas and a device for achieving the process method.

BACKGROUND ART

Chinese energy has the features of abundant coal, poor oil and deficient natural gas. Coal plays a dominant role in Chinese primary energy consumption structure. Compared with the techniques of coal-to-methanol, coal-to-dimethyl ether, and coal-to-liquid, etc., coal-to-synthetic natural gas (SNG) has a high energy efficiency (more than 60%), consumes less water by calorific value per unit, discharges less $CO_2$, has high utilization efficiency of waste heat (high temperature and high pressure steam is produced as by-product). Based on the above reasons, if the coal is used as starting material to produce the alternative natural gas by methanation reaction, the heat value of natural gas is greatly increased while the safety of transport and use thereof is improved, and the air pollution caused by the traditional coal combustion may be reduced. It meets the development direction about clean and high efficiency utilization of the coal. Meanwhile, the coal energy is clean and may be used in industry and civilian and supports the efficient use of the resourceful coal in the Chinese remote area like Xinjiang Uygur Autonomous Region and Inner Mongolia after the produced SNG is transported via the existing natural gas pipelines and go through pressure adjustment and gas mixture.

Coal-to-SNG process typically combines the coal gasification and syngas methanation. The catalytic syngas methanation is a strong exothermic reaction. Over a proper catalyst, CO could be completed converted under the optimized operation conditions. In order to maximally increase producing efficiency and operation continuity of methanation reaction device, it is the key point of fast removing way design of the heat discharged in methanation process. According to the different methods of heat removal, syngas methanation technologies could be divided into two types:

One type is sharing heat load through a plurality of adiabatic fixed-bed reactor connected in series and reducing gas temperature of reactor outlet by product gas circulation or multistage raw material gas. The representative technology includes Lurgi, TREMP™ and CRG technology, etc., which can separate mathanation reaction process from exchange heat process. To realize the separation, it needs to use many reactors and heat exchangers. Thus it increases equipment investment and has a low tolerance to raw material loads change.

The other type is methanation process integrating reaction and heat exchange. In 1970s, Germany Linda company developed a new technology of producing natural gas from coal, wherein a methanation main reactor is designed as an isothermal fixed-bed reactor, a heat exchanging pipe is installed inside a catalyst bed layer in order to remove reaction heat to produce high pressure steam, and thus the reaction is carried out under isothermal condition. However, as the heat exchanger is installed inside a fixed-bed catalyst bed layer, the catalyst particles have a higher heat transfer resistance and local overheating will occur when reaction is strong or space velocity of reaction is relatively high, which results deactivation of the catalyst. Therefore, the production efficiency is restricted greatly.

Moreover, CN101817716A discloses a new method and a device for catalytic methanation of synthesis gas. Firstly the synthesis gas realize the conversion rate of raw gas from 60% to 95% in a fluidized bed reactor. Secondly the synthesis gas enters into a fixed-bed reactor and then the final conversion rate reaches over 98% via reaction. A heat exchange pipe is installed in the fluidized bed reactor in order to remove the heat generated by the reaction and produce high quality steam as by-product. In term of the process, the method is simpler than the fixed-bed multistage adiabat reaction process. The fluidized bed reactor can realize isothermal operation to improve the space-time yield of methane. However, the catalyst particles are easy to be corroded in the fluidized bed. The catalyst particles below 200 μm have a lower operation gas velocity, which need larger volume of the reactor (especially, the reactor with the heat exchange pipe installed inside the reactor). Meanwhile a dense phase fluidized bed reactor with build-in heat exchange pipe has a larger pressure drop. Therefore, the process of fluidized-bed complete methanation is still under development in the laboratory and needs further improvement.

CN102180756A discloses a method for direct methanation of synthesis gas using a circulating fluidized bed, wherein the catalyst is fixed in the gas-solid-solid reactor. this process includes the following steps: the raw gas with inert heat carrier particles (alumina microsphere, quartz sand, florin ore sand) undergo complete methanation reaction in the gas-solid-solid reactor, the production gas and the inert heat carrier particles are separated by a cyclone separator, and the inert heat carrier particles are recirculated to the reactor. This method would sharply reduce reaction temperature and reduce carbon deposition of the catalyst.

Compared with method disclosed by CN102180756A, CN102180757A discloses a method in which the catalyst is coated on the surface of the grid inner wall of the reactor, and the inert heat carrier is replaced by the $CO_2$ absorbent (CaO/MgO). Both two methods fix the catalyst in the reactor, which inevitably corrode the catalyst because of the flow and collision between the gas and the inert heat carrier or absorbent. It is difficult to recirculate the catalyst particles and the inert heat carrier because of mixing of the catalyst particles and the inert heat carrier.

Figure 5:
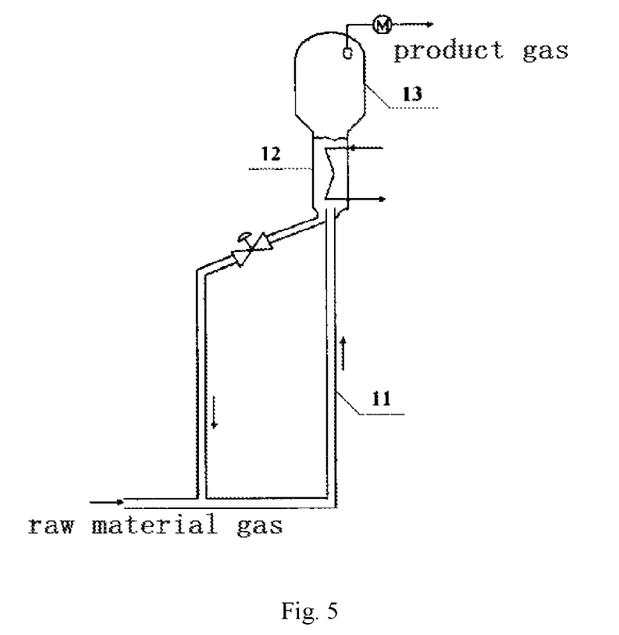
FIG. 5 is a device for circular fluidized bed in the prior art.
Figure 6:
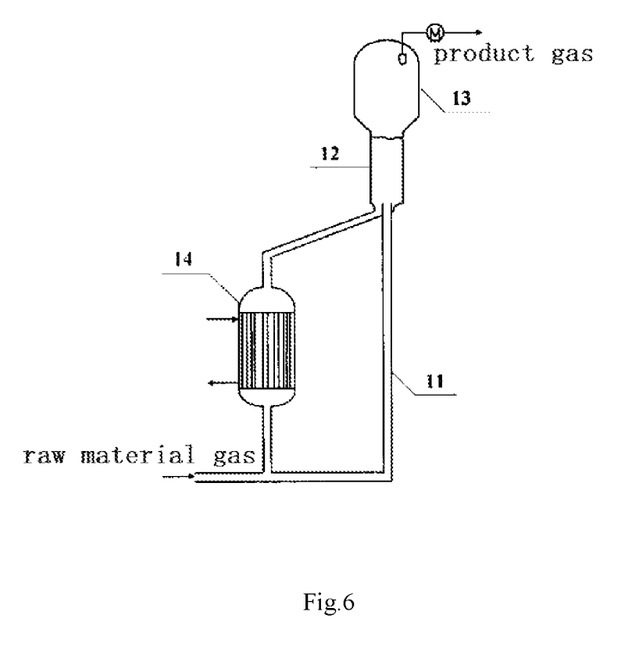
FIG. 6 is a device for circular fluidized bed in the prior art (including heat exchanger).
Figure 7:
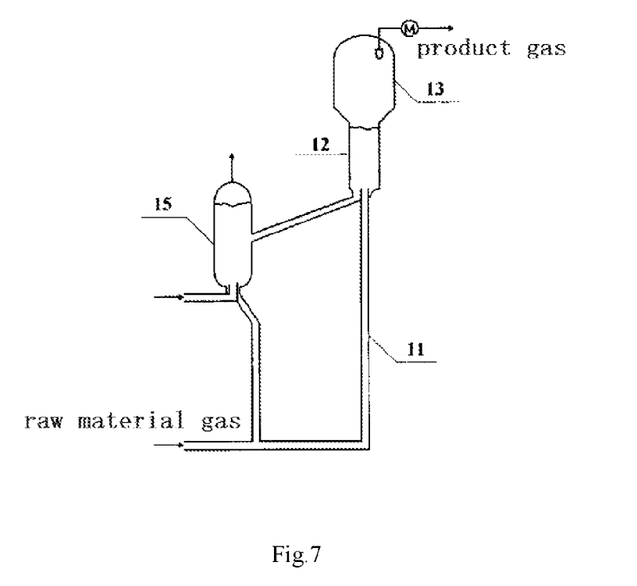
FIG. 7 is a device for circular fluidized bed in the prior art (including the fluidized bed for cooling).

JP60163828A discloses a recirculating fluidized bed device (FIGS. 5 to 7). The device is comprised of a riser 11, a dense phase fluidized bed 12, an inner cyclone separator 13, and a heat exchanger 14 or a cooling fluidized bed 15. After the synthesis gas undergoes the catalytic methanation reaction in the riser reactor, the synthesis gas and the catalyst particles concurrent flow into the dense phase fluidized bed, and then are separated into the gas and the solid by the inside cyclone separator. The catalyst particles recirculates back to the riser after being cooled via the heat exchanger or the cooling fluidized bed. Therefore, the pressure drop of the whole process (FIG. 8) is $$\Delta P = \Delta P1 + \Delta P1' + \Delta P2 + \Delta P3$$

Figure 8:
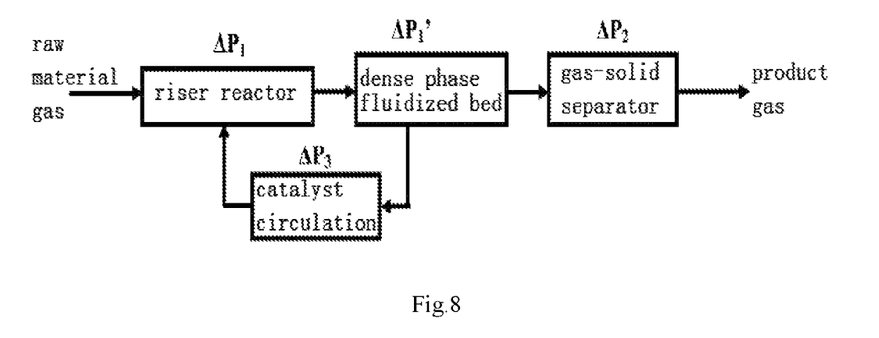
FIG. 8 is a schematic diagram of pressure drop distribution of circular fluidized bed device in the prior art; wherein
$\Delta P1$ is the pressure drop of the riser during the reaction;
$\Delta P1'$ is the pressure drop of the dense phase fluidized bed;
$\Delta P2$ is the pressure drop of the cyclone;
$\Delta P3$ is the pressure drop of the recirculating system of the catalyst particles.

Wherein
$\Delta P1$ is the pressure drop of the riser during the reaction,
$\Delta P1'$ is the pressure drop of the dense phase fluidized bed,
$\Delta P2$ is the pressure drop of the cyclone,
$\Delta P3$ is the pressure drop of catalyst recycling process.

Due to the pressure drop $\Delta P1'$ of the dense phase fluidized bed layer is relatively large, it consumes too much power. As methanation is a volume-decreasing reaction, no expanding portion would be required to reduce the catalyst entrainment.

Therefore, the process for catalytic methanation of synthesis gas is further needed to be improved.

SUMMARY OF THE INVENTION

The purpose of the invention is to provide a method for catalytic methanation of synthesis gas using an upward concurrent flow transporting bed with low pressure drop in order to solve the aforementioned technical problems.

Another purpose of the invention is to provide a device to realize the above catalytic syngas methanation method.

The method for catalytic syngas methanation comprises the following steps:

1) the synthesis gas is fed into bottom of an upward concurrent flow transporting bed reactor, the synthesis gas is fully mixed and preheated with methanation catalyst particles entering into the bottom of the upward concurrent flow transporting bed reactor, and then the mixture undergo methanation reaction after the temperature reaches the activation temperature of the catalyst;

2) after the methanation reaction is completed, product gas and the catalyst particles output from the transporting bed reactor directly enter into a gas-solid separator in order to quickly separate the product gas and the catalyst particles to obtain the product gas.

According to the method for catalytic methanation of synthesis gas of the present invention, the catalyst particles obtained by the separation in step 2) enter into a loop seal and exchange heat in a heat exchanger of the loop seal and then circulate to the transporting bed reactor.

According to the method for catalytic methanation of synthesis gas of the present invention, wherein, the catalyst is spherical Ni, Pt or Pd base catalyst with uniform particle size distribution, preferably, the spherical Ni catalyst, for example, the spherical Ni—Mg/$Al_2O_3$ catalyst prepared by spray granulation.

According to the method for catalytic methanation of synthesis gas of the present invention, wherein the activation temperature of the catalyst in step 1) is ranging from 200° C. to 300° C.

According to the method for catalytic methanation of synthesis gas of the present invention, heat-exchange tube bundles are embedded inside or a cooling water jacket is installed outside the upward concurrent flow transport bed to remove the exothermic heat of methanation in step 1).

According to the method for catalytic methanation of synthesis gas of the present invention, wherein the product gas in step 2) produces the superheated steam as the subproduct after heat exchange.

According to the method for catalytic methanation of synthesis gas of the present invention, wherein a part of the product gas circulate to the upward concurrent flow transporting bed reactor and undergo methanation reaction in order to improve the quality of the product gas.

According to the method for catalytic methanation of synthesis gas of the present invention, wherein, preferably, the outlet temperature of the upward concurrent flow transporting bed reactor is from 400° C. to 700° C., operation pressure is from 0.1 to 6.0 MPa and the gas superficial speed is from 1 to 10 m/s.

According to the method for catalytic methanation of synthesis gas of the present invention, the synthesis gas is mixture of $H_2$, CO and $CO_2$ obtained by gasification or pyrolysis of coal, biomass and petroleum coke. Preferably, the molar ratio value of $H_2$/CO is from 0.2 to 6.

According to the method for catalytic methanation of synthesis gas of the present invention, the product gas is mainly composed of the synthesis nature gas of the high calorific value including the methane.

A device for catalytic methanation of synthesis gas comprises a gas-solid separator 2 and a loop seal 3, wherein the device for catalytic methanation of synthesis gas further comprises an upward concurrent flow transporting bed reactor 1, the above device is mainly used to realize the method for catalytic methanation of synthesis gas.

An inlet of the synthesis gas and an inlet of methanation catalyst particles are disposed at bottom of the upward concurrent flow transporting bed reactor 1; top of the upward concurrent flow transporting bed reactor connects to the gas-solid separator 2; solid outlet installed at bottom of the gas-solid separator 2 connects to an inlet of the loop seal 3; outlet of the loop seal 3 connects to bottom of the upward concurrent flow transporting bed reactor 1.

The upward concurrent flow transporting bed reactor 1 is applied for catalytic methanation reaction of the synthesis gas.

The gas-solid separator 2 is preferable a cyclone separator, which is used for quickly separating the mixture of the transporting bed outlet to the product gas and the catalyst particles in. The inlet of the cyclone separator connects to the outlet of the transport bed and a lower discharged material of the cyclone separator connects to the loop seal 3. The top of the cyclone separator is the gas outlet of the methane gas.

The loop seal 3 is used for storing and recycling the catalyst particles, and the catalyst particles circulate to the bottom of the transporting bed for keeping the circulating amount of the catalyst stable. The bottom of the material loop seal 3 connects to the bottom of the upward concurrent flow transporting bed reactor 1 via the inverted V type valve or slide valve.

According to the device for catalytic methanation of synthesis gas of the present invention, a heat transfer pipe 6 is embedded inside the upward concurrent flow transporting bed reactor 1.

According to the device for catalytic methanation of synthesis gas of the present invention, a water jacket 7 is installed outside the upward concurrent flow transporting bed reactor 1.

The heat transfer pipe and the water jacket are used for transferring the exothermic heat in the methanation reaction for other application.

According to the device for catalytic methanation of synthesis gas of the present invention, another outlet is disposed at gas outlet of the gas-solid separator 2 and connects to a gas input pipe of the upward concurrent flow transporting bed reactor 1 through a gas circulating pipe 8. The product gas output from the gas-solid separator 2 partly circulate to the upward concurrent flow transporting bed reactor and undergo reaction in order to improve the quality of the product gas.

According to the device for catalytic methanation of synthesis gas of the present invention, a heat exchanger 4 is installed inside the loop seal 3, which is used to reduce the temperature of the catalyst particles and produce the overheat steam.

According to the device for catalytic methanation of synthesis gas of the present invention, a second heat exchanger 5 is preferable disposed at the gas outlet of the gas-solid separator 2, the overheat stream is produced as by-product after heat exchange.

In conclusion, the present invention provides a process and device for catalytic methanation of synthesis gas using the upward concurrent flow transporting bed reactor, which has the following advantages:

Firstly, the invention employs the upward concurrent flow transporting bed reactor as the methanation reactor. Compared with the fixed bed reactor, the relative movement between the catalyst particles and the fluid is frequent and powerful; heat transfer efficiency and gas-solid mass transfer are high; heat removal is convenient; bed layer temperature is easily controlled; utilization efficiency of the catalyst is improved. The device is simple, easy to operate. Due to the high gas superficial speed in the upward concurrent flow transporting bed and relatively smaller diameter compared with the ordinary fluidized bed reactor, the reactor is of low pressure drop and power consumption.

Figure 9:
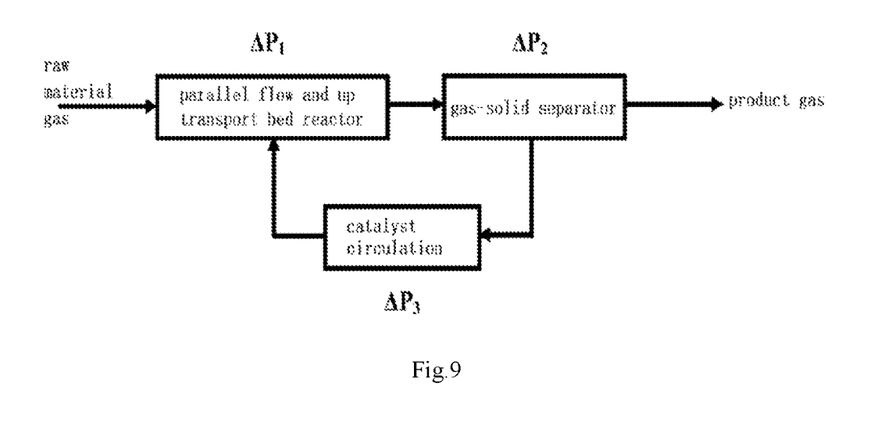
FIG. 9 is a schematic diagram of pressure drop distribution of the device for catalytic methanation of synthesis gas of the present invention; wherein,
$\Delta P1$ is the pressure drop of the transporting bed reactor during the reaction;
$\Delta P2$ is the pressure drop of a gas-solid separator;
$\Delta P3$ is the pressure drop of the recirculating system of catalyst particles.

Secondly, the synthesis gas directly enters into the separator to separate the product gas from the catalyst particles after catalytic methanation reaction in the upward concurrent flow transporting bed reactor is completed. Different from that the product gas and the catalyst particles firstly concurrently enter into the dense phase fluidized bed and then secondly separate gas from solid in built-in cyclone separator (refer to JP60163828A), it can obviously reduce the pressure drop of the process (please see the FIG. 9, $\Delta P = \Delta P1 + \Delta P2 + \Delta P3$).

Thirdly, the outlet temperature of the transporting bed can reach 700° C. The product gas and the catalyst particles separated by the gas-solid separator can produce overheat steam via heat exchange in order to improve the energy utilization efficiency of the whole process.

Fourthly, the invention provides a process for catalytic methanation of synthesis gas using the transporting bed, which can control reaction temperature and reaction time to make it suitable for the gas-solid reaction characterized by the other quick and strong heat emission.

The drawing reference number:
1 the upward concurrent transporting bed reactor 2 the gas-solid separator
3 the loop seal 4 the first heat exchanger
5 the second heat exchanger 6 the heat transferring pipe
7 the water jacket 8 the gas circulating pipe
11 the riser 12 the dense phase fluidized bed
13 the inner cyclone separator 14 the heat exchanger
15 the cooling fluidized bed

DETAILED DESCRIPTION OF THE EMBODIMENT

A further description of the present invention will be provided in conjunction with drawings and the embodiments.

Embodiment 1

Figure 1:
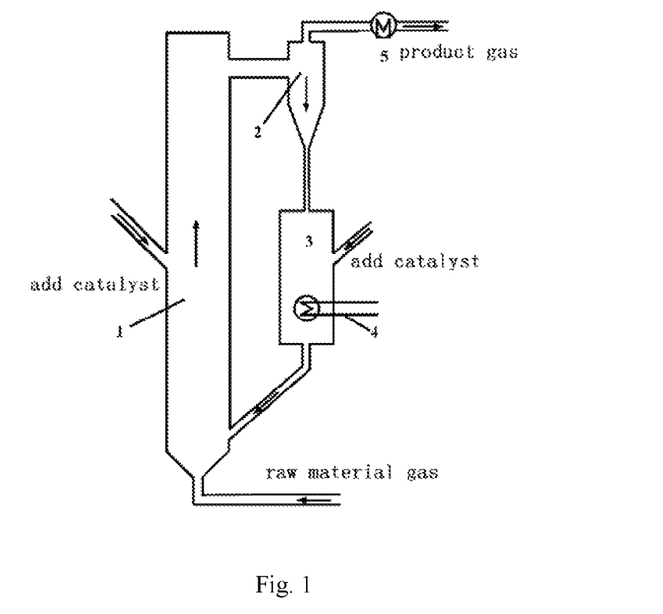
FIG. 1 is a diagram of the reaction device for catalytic methanation of synthesis gas using a transporting bed with low pressure drop used in embodiment 1 of the present invention.

The embodiment provides a method for catalytic methanation of the synthesis gas using a transporting bed with low pressure drop. The reaction device is as shown in FIG. 1.

The catalyst used in the device of the present invention is the spherical particle catalyst with the diameters of 60-100 µm. The component and content of the reaction products are analyzed by Micro 3000 (Agilgent) gas-phase chromatograph. The reaction transformation rate and the methane selectivity are computed as the following formula:

CO transformation rate (%)=the amount of the transferred CO converted/the amount of the CO included in the material gas×100%;

Methane selectivity (%)=the amount of the $CH_4$ yielded/the amount of the converted CO×100%;

The material gas ($H_2$:CO=3:1) and the catalyst particles are strongly mixed and preheated to 300° C. at the bottom of the transporting bed. They undergo the methanation reaction in an upward concurrent flow transporting bed reactor 1 with an operation pressure of 0.1 MPa, a gas superficial speed of 1 m/s and an outlet temperature of 640-645° C. The final reaction transformation rate reaches 55%-62% while the methane selectivity reaches 68%-70%. Gas-solid mixture output from reactor outlet is quickly separated into product gas and the catalyst via a gas-solid separator 2. The separated high temperature catalyst particles undergo heat exchange in a first heat exchanger 4 inside a loop seal 3 and then enter into the transporting bed to undergo circulation. The lower end of the loop seal connects to the bottom of the transporting bed via particles seal and the structure of the inverted V valve type in order to protect the gas inside the transporting bed from entering into the loop seal 3 to keep the system stable. The product gas discharged from the top of the gas-solid separator 2 undergo heat exchange inside a second heat exchanger 5 and then enter into a purification device in the subsequent process to obtain the synthesis nature gas of the high heat value including methane.

Embodiment 2

Figure 2:
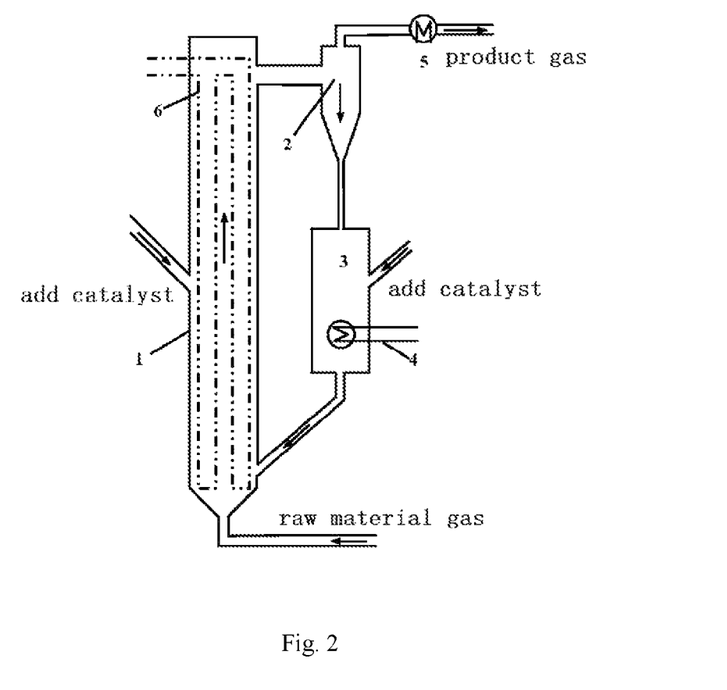
FIG. 2 is a diagram of the reaction device for catalytic methanation of synthesis gas using a transporting bed with low pressure drop in embodiment 2 of the present invention (heat transfer pipe being installed inside the transporting bed).

The embodiment provides a method for catalytic methanation of the synthesis gas using the transporting bed with low pressure drop, wherein a heat transfer pipe 6 is installed inside the transporting bed reactor 1 in order to remove the exothermic heat of methanation. The detailed device is as shown in FIG. 2.

The raw material gas ($H_2:CO=3:1$) and the catalyst particles are strongly mixed and preheated to 300° C. at the bottom of the transporting bed. They undergo the methanation reaction in the transporting bed reactor 1 with an operation pressure in the reactor of 0.1 MPa, a gas superficial speed of 1 m/s, and an outlet temperature of the reactor of 400-410° C. via adjusted by the heat transfer pipe 6 inside the transporting bed. The final reaction transformation rate reaches 80%-85% while the methane selectivity reaches 81%-84%. Gas-solid mixture output from reactor outlet is quickly separated into product gas and catalyst via a gas-solid separator 2. The separated high temperature catalyst particles undergo heat exchange in the first heat exchanger 4 inside the loop seal 3 and then enter into the transporting bed to undergo circulation. The lower end of the loop seal connects to the bottom of the transporting bed via particles seal and the structure of the inverted V valve type in order to protect the gas inside the transporting bed from entering into the loop seal 3 to keep the system stable. The product gas discharged from the top of the separator undergo heat exchange inside the second heat exchanger 5 and then enter into the purification device in the subsequent process to obtain the synthesis nature gas of the high heat value including methane.

Embodiment 3

The embodiment provides a method for catalytic methanation of the synthesis gas using the transporting bed with low pressure drop, wherein, the water jacket 7 is installed outside the transporting bed reactor in order to remove the heat discharged during methanation reaction. The detailed device is as shown in the FIG. 3.

Figure 3:
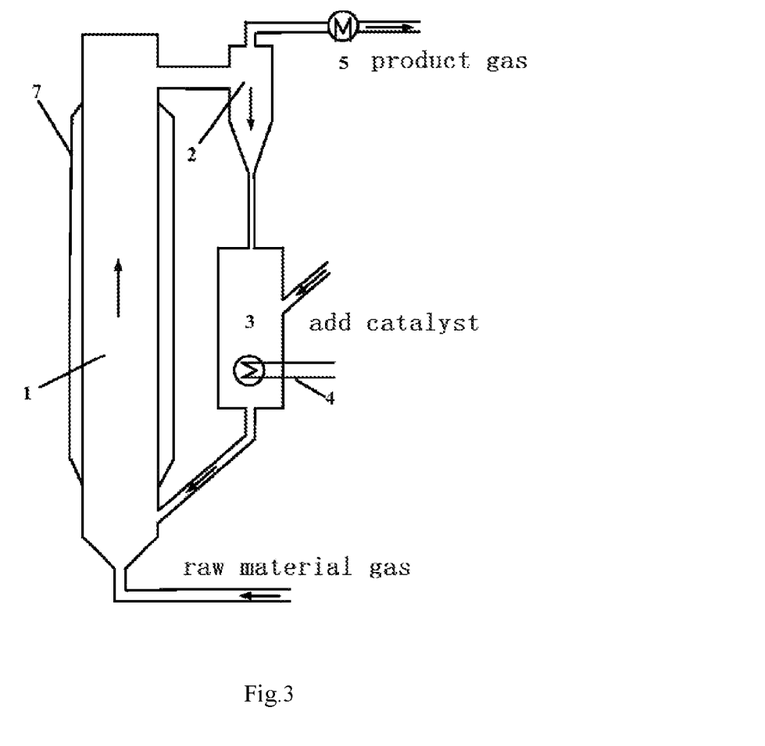
FIG. 3 is a diagram of the reaction device for catalytic methanation of synthesis gas using a transporting bed with low pressure drop used in embodiment 3 of the present invention (water jacket being provided at the outside of the transporting bed).

The material gas and the catalyst particles are strongly mixed and preheated to 300° C. at the bottom of the transporting bed. They undergo the methanation reaction in the transporting bed reactor 1 with an operation pressure in the reactor of 0.1 MPa, a gas superficial speed of 1 m/s, and an outlet temperature of the reactor of 400-410° C. adjusted by the import and export water of the water jacket 7 outside the transporting bed. The final reaction transformation rate reaches 80%-85% while the methane selectivity reaches 81%-84%. Gas-solid mixture of reactor outlet is quickly separated into product gas and catalyst via the gas-solid separator 2. The separated high temperature catalyst particles undergo heat exchange in the first heat exchanger 4 inside the loop seal 3 and then enter into the transporting bed to undergo circulation. The lower end of the loop seal connects to the bottom of the transporting bed via particles seal and the structure of the inverted V valve type in order to protect the gas inside the transporting bed from entering into the loop seal 3 to keep the system stable. The product gas discharged from the top of the separator is undergo heat exchange inside the second heat exchanger 5 and then enter into the purification device in the subsequent process to obtain the synthesis gas of the high heat value including methane.

Embodiment 4

The embodiment provides a method for catalytic methanation of the synthesis gas using the transporting bed with low pressure drop. A portion of the product gas need to circulate to the transporting bed to continue undergoing methanation reaction in order to improve the quality of the product gas. The detailed device is as shown in the FIG. 4.

Figure 4:
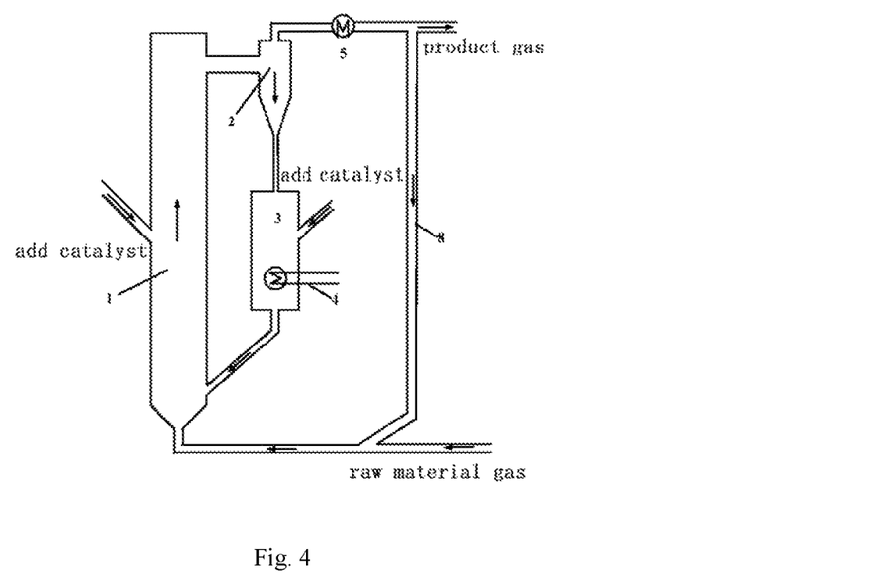
FIG. 4 is a diagram of the reaction device for catalytic methanation of synthesis gas using a transporting bed with low pressure drop used in embodiment 4 of the present invention (the circulation of the product gas).

The material gas ($H_2:CO=3:1$) and the catalyst particles are strongly mixed and preheated to 300° C. at the bottom of the transporting bed. They undergo the methanation reaction in the transporting bed reactor 1 with an operation pressure in the reactor of 0.1 MPa, and a gas superficial speed of 1 m/s, and an outlet temperature of the reactor of 520-532° C. The final reaction transformation rate reaches 86%-87% while the methane selectivity reaches 78%-80%. Gas-solid mixture of reactor outlet is quickly separated into product gas and catalyst via the gas-solid separator 2. The separated high temperature catalyst particles undergo heat exchange in the first heat exchanger 4 inside the loop seal 3 and then enter into the transporting bed to undergo circulation. The lower end of the loop seal connects to the bottom of the transporting bed via particles seal and the structure of the inverted V valve type in order to protect the gas inside the transporting bed from entering into the loop seal 3 to keep the system stable. The product gas discharged from the top of the separator undergo heat exchange inside the second heat exchanger 5, and then one part of the product gas circulate to the transporting bed to continue to undergo methanation reaction via a gas circulating pipe 8, and the other part of the product gas enters into the purification device in the subsequent process in order to obtain the synthesis gas of the high heat value including methane.

What is claimed is:

1. A method for catalytic methanation of synthesis gas, the method comprising the steps of:
   1) the synthesis gas is fed into bottom of an upward concurrent flow transporting bed reactor, the synthesis gas is fully mixed and preheated with methanation catalyst particles entering into the bottom of the upward concurrent flow transporting bed reactor, and then the mixture undergo methanation reaction after the temperature reaches the activation temperature of the catalyst, wherein outlet temperature of the upward concurrent flow transporting bed reactor is from 400° C. to 700° C., operation pressure is from 0.1 to 6.0 MPa and gas superficial speed is from 1 to 10 m/s;
   2) after the methanation reaction is completed, product gas and the catalyst particles output from the transporting bed reactor directly enter into a gas-solid separator in order to quickly separate the product gas and the catalyst particles to obtain the product gas.

2. The method for catalytic methanation of synthesis gas according to claim 1, wherein the catalyst particles obtained by the separation in step 2) enter into a loop seal and exchange heat in a heat exchanger of the loop seal and then circulate to the transporting bed reactor.

3. The method for catalytic methanation of synthesis gas according to claim 1, wherein heat-exchange tube bundles are embedded inside or a cooling water jacket is installed outside the upward concurrent flow transport bed to remove the exothermic heat of methanation in step 1).

4. The method for catalytic methanation of synthesis gas according to claim 1, wherein the product gas in step 2) produces overheated steam as sub-product after heat exchange via a heat exchanger.

\* \* \* \* \*